United States Patent [19]

Yapel, Jr.

[11] 4,147,767

[45] Apr. 3, 1979

[54] ALBUMIN MEDICAMENT CARRIER SYSTEM

[75] Inventor: Anthony F. Yapel, Jr., Saint Paul, Minn.

[73] Assignee: Minnesota Mining and Manufacturing Company, Saint Paul, Minn.

[21] Appl. No.: 838,355

[22] Filed: Sep. 30, 1977

Related U.S. Application Data

[63] Continuation-in-part of Ser. No. 621,145, Oct. 9, 1975, abandoned.

[51] Int. Cl.$^2$ .............................................. A61K 9/50
[52] U.S. Cl. ...................................... 424/22; 424/19; 424/36; 252/316
[58] Field of Search ............................. 424/36, 19–22; 252/316

[56] References Cited

U.S. PATENT DOCUMENTS

| | | | |
|---|---|---|---|
| 3,043,782 | 7/1962 | Jenson | 252/316 |
| 3,265,629 | 8/1966 | Jenson | 252/316 |
| 3,265,630 | 8/1966 | Jenson | 252/316 |
| 3,533,958 | 10/1970 | Yurkowitz | 252/316 |
| 3,541,201 | 11/1970 | Brown | 424/7 |
| 3,663,685 | 5/1972 | Evans | 424/1 |
| 3,663,686 | 5/1972 | Grotenhuls | 424/1 |
| 3,663,687 | 5/1972 | Evans | 424/1 |
| 3,937,668 | 2/1976 | Zolle | 252/316 |

*Primary Examiner*—Shep K. Rose
*Attorney, Agent, or Firm*—Cruzan Alexander; Donald M. Sell; Carolyn A. Bates

[57] ABSTRACT

Solid serum albumin spherules having 5 to 30 percent by weight of an organic medicament homogeneously entrapped therein are disclosed. These spherules are especially suited for intravascular injection into the body wherein the drug is released from the spherule in a biphasic manner having an initial fast release phase followed by a slow release phase.

18 Claims, 2 Drawing Figures

ALBUMIN MEDICAMENT CARRIER SYSTEM

RELATED APPLICATIONS

This application is a continuation-in-part of application Ser. No. 621,145 filed Oct. 9, 1975, now abandoned.

BACKGROUND OF THE INVENTION

This invention relates broadly to the art of drug formulation. Specifically, it relates to the art of formulating drugs in an inert carrier matrix which is suspendable in a liquid and suitable for parenteral injection into the body. More specifically it relates to the entrapment of drugs in a porous carrier matrix which provides controlled release of the drug following its introduction into the body.

DESCRIPTION OF THE PRIOR ART

Medical Science has long recognized the need for an effective way to control the release of drugs in the body so that a drug may be administered less frequently while at the same time providing continuous therapeutic levels of the drug in the patient's blood stream.

Attempts to control drug release have been somewhat successful when the drug is administered orally or by implants. Various coatings and capsules have been developed to surround the drug and retard its release.

Controlled release of drugs administered parenterally, especially those administered intravascularly, has presented greater problems.

Ordinarily, intravascular injection requires careful control of drug dosage. Because the drug becomes immediately available to the body upon intravascular injection, overdoses of toxic drugs can cause serious complications. The intravascular route has also been limited to the administration of soluble drugs because of the danger of embolism formation when insoluble particles are injected.

British Pat. No. 931,532 describes a method of microencapsulating drugs in a gelable hydrophilic colloid by a process of complex coacervation. The colloid forms a membrane around the drug nucleus. It is suggested that the permeability of the membrane can be structured so as to permit gradual release of the drug.

U.S. Pat. No. 3,541,201 describes an injectable substance whereby an active drug is incorporated in the internal structure of a metabolizable "protein-like" carrier. The carrier particles are injected as a suspension in a suitable non-aqueous vehicle. The metabolizable carrier particle is acted upon by the enzymes of the body fluids, and the incorporated drugs are released slowly as a result thereof.

U.S. Pat. Nos. 3,773,919 and 3,887,699 describe formulations of polylactide and drug which can be parenterally administered and provide a slow, sustained release of the drug over a period of time.

A major problem associated with slow release injectable drug formulations of the prior art is that the release rate of the drug often does not correspond to the therapeutic needs of the patient. It is well known in the medical art that in order for a drug to produce the maximum therapeutic effect it must reach an optimum concentration in the patient's blood stream. Thus, physicians often administer a high initial dose or "loading dose" of the drug to reach this concentration in the blood stream. Following the loading dose, subsequent doses are administered to maintain this level. The time between doses is determined by the rate of metabolism of the drug.

Thus, the ideal sustained release drug formulation should provide a biphasic release of the drug. An initial fast release phase is desirable to provide therapeutic concentrations in the blood stream, and a subsequent slow release phase is necessary to maintain blood levels of the drug and keep pace with the drug's metabolism by the body.

Prior art injectable drug formulations generally do not provide such a biphasic release system. Instead the release rates are monophasic with the drug being released gradually and constantly over a period of time.

The albumin medicament carrier system of the present invention effectively solves this deficiency of the prior art and provides a unique biphasic drug release system. The present system provides an adjustable initial rapid release of the entrapped drug followed by an adjustable secondary slow release phase.

The use of albumin as a carrier or complexing agent for medicaments has been known at least since 1899. In recent years, spherules of serum albumin have been used as carriers for radioactive diagnostic and therapeutic agents. These spherules are described in U.S. Pat. Nos. 3,663,685, 3,663,686, and 3,663,687. However, these patents do not disclose that these spherules have the unique ability to release entrapped medicaments in a biphasic manner when crosslinked at temperatures of 110° to 180° C. for at least twenty minutes or equivalently crosslinked by chemical means.

DESCRIPTION OF THE INVENTION

The present invention provides a therapeutic composition for controlling the release of drugs comprising solid serum albumin spherules having homogeneously entrapped therein from 5 to 30 percent by weight of the spherule of an organic medicament which is at least 0.01 percent water-soluble at 37° C. The spherules must be subjected during their preparation to temperatures between 110° to 180° C. for a minimum of twenty minutes to crosslink the albumin, or equivalently crosslinked by chemical crosslinking agents. When placed in an aqueous medium, the medicament is released from the spherules in a biphasic manner as defined hereinbelow. As will be demonstrated, the degree of heat or chemical crosslinking of the spherules as well as the concentration level of drug within the spherules is important to achieving biphasic release of the entrapped drug.

In addition to the advantageous biphasic drug release provided by the albumin medicament carrier system of the present invention, there are several other important features of the system. The size of the spherules can be carefully controlled during processing, and spherule size can be utilized to direct the spherules to a particular part of the body. For example, spherules of 10-100 microns in diameter are readily deposited in the capillary bed of the lung following intravenous injection. Thus, drug-containing spherules in this size range can be conveniently used to treat disorders of the lung, such as asthma, tuberculosis, pneumonia, tumors, etc.

Similarly, spherules of 1-5 microns in diameter can be used to deliver drugs to the liver. Intra-arterial injection or catheterization can be used to direct the spherules to the capillary systems of other organs or to tumors.

There are obvious advantages to localizing the drug in the capillaries of the organ or tumor to be treated. The drug is released directly to the intended site and toxic side effects to other tissues are likely to be reduced. This feature makes the present system particularly useful in treating tumors with anti-neoplastic drugs which are generally highly toxic to healthy as well as malignant tissue.

This delivery system, however, is not restricted to the treatment of tumors or diseased organs. For example, either the healthy lung or liver can be utilized as a conveniently reached depot or reservoir for the spherule from which an appropriate drug could be dispensed systemically to the body over an extended period of time.

An especially important advantage of this delivery system is the absence of emboli formation when albumin carrier spherules are administered intravascularly. Water insoluble drugs which formerly could not be administered in this manner because of the risk of embolus formation can be safely given by entrapping them in albumin spherules.

Other advantages of albumin spherules as medicament carriers in the present invention include their ease of preparation, complete removal from the body by metabolism, nonantigenicity, proven safety for intravascular administration, capability of accommodating a wide variety of drug molecules in a relatively nonspecific fashion, as well as other advantages which shall become apparent upon further disclosure of the invention.

The carrier material used in the system of the invention is serum albumin. When treating human patients, human serum albumin is used, and when treating other animals, the serum albumin should likewise be species-specific, e.g., bovine serum albumin for treating cattle. Species-specific serum albumin is necessary for compatibility reasons.

The term "medicament" as used herein refers broadly to non-radioactive, organic molecules used in the medical art to treat diseases or disorders of the body.

The water-solubility of the medicament is largely unimportant to the practice of the invention within broad limits. However, if the drug is quite water-insoluble, i.e., less than 0.01 percent water soluble at 37° C., it will be released very slowly from the albumin spherule and the biphasic release properties of the spherule are less apparent.

The concentration of the drug in the spherule is critical to achieving biphasic release of the drug from the spherules. Drug loadings below about 5 percent where the drug is homogeneously dispersed in a matrix are generally therapeutically inadequate unless an undesirably large number of spherules are administered. When drug loadings exceed about 30 percent, it has been observed that the biphasic release characteristics of the spherules are greatly diminished, i.e., the slow release phase and the fast release phase become indistinguishable.

Listed below are some of the many types of drug classes and specific examples of each which have been incorporated into serum albumin spherules according to the present invention.

| DRUG CLASS | EXAMPLES |
| --- | --- |
| Anti-asthmatics | Intal (disodium cromoglycate) |
| Analgesics | Morphine |
|  | Codeine |
|  | Sodium salicylate, salicylic acid |
|  | Meperidine hydrochloride (Demerol ®) |
| Antitussives | Codeine |
|  | Chlophedianol hydrochloride |

| DRUG CLASS | EXAMPLES |
| --- | --- |
| Bronchodilators | Epinephrine |
|  | Isoproterenol |
|  | Salbutamol |
|  | Terbutaline |
|  | Ephedrine |
|  | Aminophylline |
| Narcotics | Morphine |
|  | Codeine |
|  | Cocaine |
|  | Meperidine hydrochloride (Demerol ®) |
| Mucolytic agents | Acetylcysteine |
| Antibacterials | Sulfanilamide |
|  | Sulfadiazine |
|  | Tetracycline |
| Antituberculars | Rifampin (rifamycin) |
|  | Dihydrostreptomycin |
|  | p-aminosalicylic acid |
| Hypoglycemics | Tolbutamide (Orinase ®) |
|  | Insulin |
| Steroids | Hydrocortisone |
|  | Prednisone |
|  | Prednisolone |
|  | Prednisolone metasulfobenzoate |
| Antitumor agents | Chlorambucil |
|  | Busulfan |
|  | Alkaloids |
|  | Colchicine |
|  | Antimetabolites |
|  | 6-mercaptopurine |
|  | Thioguanine |
|  | 5-fluorouracil |
|  | Hydroxyurea |
|  | Adriamycin ® |
| Amino Acids | Methionine |

The rate at which the drug is released from the albumin spherule is largely dependent upon the degree to which the albumin is crosslinked during preparation. As will be described in detail hereinbelow, the albumin can be crosslinked by either heat treatment or by chemical crosslinking agents.

In addition to the degree of crosslinking of the albumin various other factors will influence the release rate of a particular drug. These factors include the molecular weight of the drug, its water solubility, and any electrostatic or hydrophobic interactions between the drug and the albumin.

The concentration of the albumin solution used to prepare the spherules will also have some effect on ultimate drug release characteristics. Typically, spherules are prepared from a 20-50 percent solution (w/v) of the albumin in water. Spherules have been prepared from solutions as low as 2-5 percent in protein concentration and as high as 70-80 percent. In general, and particularly for heat crosslinked spherules, those spherules prepared from the higher concentration solutions are more dense and release incorporated drugs somewhat more slowly than those prepared from lower concentration solutions, all other things being equal.

In general, a given weight of very thin microspheres (e.g., 1-5 microns) containing a specific amount of a drug will release that drug faster than the same weight of larger microspheres (e.g., 50-100 microns) containing the same amount of drug because of the much larger surface area of the smaller spheres. Hence, all other things being equal, smaller microspheres will generally release drug faster than larger microspheres strictly on the basis of surface area considerations. Thus, variations in sphere size can be used along with the other parameters discussed above to help regulate drug release rates from albumin spherules.

Although the above factors will affect the release rates of individual drugs from albumin microspheres, the properties of the albumin itself when crosslinked to the degree specified will cause the drug to be unexpectedly released in a biphasic manner.

The process for preparing the spherules of the invention is essentially that described by Evans in U.S. Pat. No. 3,663,687 for preparing precursor albumin spherules, although several improvements in this process have been discovered.

According to the process, the selected drug is dissolved or dispersed directly in an aqueous solution of the serum albumin at the desired concentration level. The concentration of albumin in the aqueous solution will generally range from about 20 to 60 percent (w/v). Drug concentrations in the albumin solution will range from 5 to 30 percent of the weight of albumin. To ensure uniform, homogeneous distribution of highly water-insoluble drugs in the albumin solution, the drugs should be ball-milled or micronized prior to dispersion in the solution.

Following addition of the drug to the albumin solution, the mixture is allowed to equilibrate for a period of time ranging from 15 to 60 minutes. During this equilibration step, a certain percentage of the drug molecules may be bound to sites on the albumin molecules. The actual amount of drug bound will depend on such factors as the nature of the binding sites on the albumin, the amount and polarity of the electrostatic charge, if any, on the carrier and drug, the concentration of both drug and carrier in the equilibrating solution, the equilibrium constant between carrier sites and drug molecules, the temperature, and other mass-law considerations.

To prepare spherules by the entrapment technique, the aqueous albumin solution containing dissolved or dispersed drug is injected through a 20 or 25 gauge hypodermic needle into a bath of vegetable oil being rapidly stirred at 500–2500 rpm. While stirring is continued, the oil bath is typically heated to a temperature of 110° to 180° C. over a period of 15 to 30 minutes and then held at this temperature for a period of at least 20 minutes. Heat treatments in excess of ten hours are generally not required. During this heating process, which results in internal crosslinking and ultimate insolubilization of the carrier spheres, that portion of the insoluble drug or excess soluble drug not chemically bound to actual sites on the protein carrier is entrapped or incorporated within interstices between the carrier chains forming the three dimensional spherule structure. This "stir-heat" procedure carried out under the conditions outlined above produces water-insoluble spherules 5 to 80 microns in diameter. The particle size range of the spheres can be controlled by varying the rate of injection of the drug-carrier solution or dispersion into the oil bath and/or by varying the stirring speed of the oil bath. The addition of small amounts (0.1 to 2 percent) of surfactant (e.g., Tween®80, Pluronic®F-68) to the starting albumin solutions will also influence ultimate spherule size through its indirect effects on surface and interfacial tensions. The biodegradability and porosity of the spherules can be controlled by varying the time and temperature of the heating process in oil. Other things being equal, higher temperatures and longer heating times generally produce harder, less porous, and more slowly degradable spherules. When the desired degree of spherule insolubilization has been obtained, the oil bath is cooled either in air or ice water and the spherules are removed from the oil by ultrafiltration or suction on a 0.45 micron pore size Millipore filter or Whatman #5 filter paper. Several subsequent washes of the spherules with heptane and/or ether remove any remaining oil from the spherule surface. After air-drying, the drug-containing spherules are obtained as a free-flowing powder whose color varies in accordance with the color of the incorporated drug or drugs. For intravascular injection, the spherules are suspended in a pharmaceutically-acceptable extending medium suitable for intravascular injection.

The heat insolubilization technique discussed above is particularly advantageous in that it is possible to incorporate both dispersions of water-insoluble drugs as well as solutions of water-soluble drugs by entrapment. Despite its many advantages, there is one drawback to the heat-in-solubilization method, and this relates to the fact that during the spherule formation and drug entrapment procedure, the spherules must often be heated to temperatures in excess of 110° C. Although high temperatures may be of little consequence for highly stable drugs, they may lead to degradation and loss of drug efficacy in the case of less stable drugs. To alleviate this problem room temperature insolubilizing techniques have been developed.

These room temperature insolubilizing techniques involve the use of chemical crosslinking agents, particularly formaldehyde and glutaraldehyde which are excellent hardening agents for albumin.

It has been found that lipophilic drying alcohols such as n-butanol, sec-butanol and 2-ethylhexanol can be readily dissolved in vegetable oil such as cottonseed oil, a standard spheroidizing bath medium. Water-soluble crosslinking agents like formaldehyde and glutaraldehyde can be dissolved in the drying alcohols. In particular, up to 25 percent (by volume) of the water-soluble crosslinking agents glutaraldehyde (in the form of a 25 percent aqueous solution) or formaldehyde (in the form of a 37 percent aqueous solution) can be dissolved in a lipophilic drying alcohol like n-butanol. If approximately 1 to 40 parts (by volume) of such a glutaraldehyde/butanol or formaldehyde/butanol solution are mixed with 70 to 500 parts cottonseed oil, a bath solution containing both dissolved crosslinking agent and drying alcohol is obtained. If an aqueous solution of 25 to 50 percent serum albumin is now injected into this bath while stirring at approximately 1200 to 1500 rpm, spherules in the 20 to 100 micron size range are produced. (Smaller spherules can be obtained by employing faster stirring speeds or by decreasing the concentration of carrier in the original solution injected into the bath). The solvent water within the spherules partitions into the drying alcohol while the spherules themselves are crosslinked by the glutaraldehyde or formaldehyde. The spherules are filtered from the preparation bath after at least 20 minutes of contact with the crosslinking medium, and the drug release characteristics of the spherules are similar to those produced by heat insolubilization. The degree of spherule crosslinking can be controlled by varying the time that the spherules are kept in contact with the crosslinking agent and by varying the amount of crosslinking agent in the preparation bath.

The above process is particularly advantageous in that carrier spheroidization, dewatering, and crosslinking can be accomplished in a single convenient step. If the crosslinking agent is omitted in the above procedure, chemically dewatered, dry, free-flowing albumin microspheres will result which dissolve on contact with water.

The room temperature preparation method is particularly useful for entrapping heat-sensitive water-soluble or water-insoluble drugs, although it may be used for heat stable drugs also. A modification of this technique can also be used for drugs which can be safely heated to temperatures of up to 105° C.

According to this modified chemical crosslinking process, the albumin-drug mixture is injected into a low temperature bath (less than 105° C.) and the spherules are partially insolubilized. Alternatively, the albumin-drug mixture can be spheroidized and chemically dewatered without crosslinking as discussed above. The resulting spherules are isolated and placed in a desiccator and exposed to vapors of glutaraldehyde or formaldehyde for a minimum of twenty minutes. The formaldehyde and/or glutaraldehyde can be placed in the bottom of the desiccator in the form of commercially available 37 percent and 25 percent aqueous solutions, respectively. Aldehyde vapor treatments can be continued up to several days with continued exposure leading to denser, less porous, more water-insoluble spheres. After vapor crosslinking, excess formaldehyde or glutaraldehyde can be readily removed from the treated microspheres by aspiration or vacuum desiccation.

In addition to formaldehyde and glutaraldehyde crosslinking agents, which are preferred, other crosslinking agents may be utilized in preparing the albumin spherules of the invention. For example, di-, tri- and tetravalent metallic cations may be used. Cations such as $Fe^{3+}$, $Al^{3+}$ and the like can be readily dissolved in n-butanol, sec-butanol, 2-ethylhexanol and other lipophilic drying alcohols which in turn can be dissolved in cottonseed or other vegetable oils. The resulting solution serves as a one-step crosslinking bath for albumin carrier spherules.

Other protein crosslinking agents are known in the art and can be utilized as suitable alternative crosslinking agents. Some of these are listed in the following table.

| Crosslinking Agent | Water Solubility | Reacts Primarily with Following Groups In Protein |
| --- | --- | --- |
| 3,6-Bis(mercurimethyl)-dioxane | Soluble | Sulfhydryl |
| N,N'-(1,3-phenylene)bismaleimide | Insoluble | Sulfhydryl |
| N,N'-Ethylene-bis-(iodoacetamide) | Soluble | Sulfhydryl |
| 1,5-Difluoro-2,4-dinitrobenzene | Insoluble | Amino groups, tyrosine |
| p,p'-Difluoro-m,m'-dinitrodiphenyl sulfone | Insoluble | Amino groups, phenol groups |
| Dimethyl adipimidate | Soluble | Amino groups |
| Phenol-2,4-disulfonyl chloride | Soluble | Amino groups |
| Hexamethylenediisocyanate $O=C=N-CH_2-(CH_2)_4-CH_2-N=C=O$ | Insoluble | Amino groups |
| Woodward's reagent K | Soluble | Links carboxyl and amino groups |

| Crosslinking Agent | Water Solubility | Reacts Primarily with Following Groups In Protein |
|---|---|---|
| [structure with SO3−, CH, CH, N+—CH2—CH3, O] | | |
| Bisdiazobenzidine  [+N2—⟨⟩—⟨⟩—N2+] | Soluble | Tyrosine, histidine |

The water-insoluble reagents listed above may be dissolved directly in the stirred, hydrophobic oil bath and utilized in this form to crosslink albumin spherules formed following injection of an aqueous solution of the albumin into the bath. Water-soluble crosslinking agents may be incorporated directly into the aqueous albumin solution or solubilized in the alcohol which functions as a dewatering agent when resident in the oil.

Obviously, combinations of heat and chemical crosslinking techniques can be utilized to achieve the desired drug release properties of the albumin spherules of the invention.

DESCRIPTION OF THE DRAWINGS

Understanding of the biphasic release characteristics of the spherules may be facilitated by reference to the accompanying drawings wherein.

Figure 1:
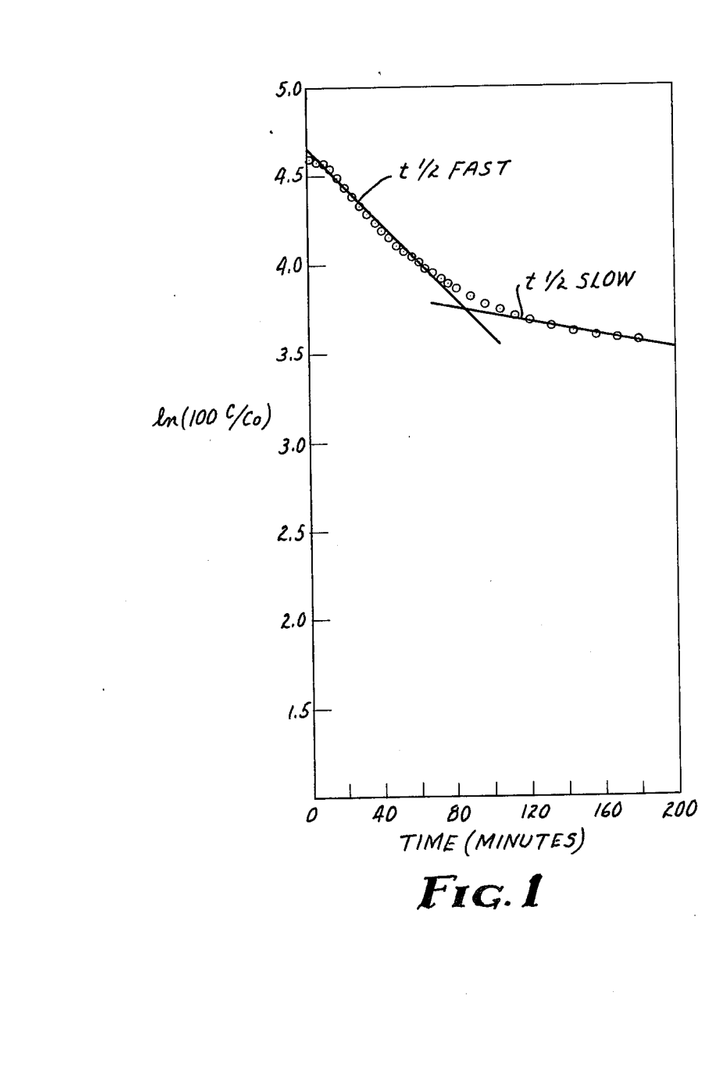
FIG. 1 is a typical drug release curve obtained with human albumin spherules containing 9.1 percent by weight of the drug epinephrine.

The spherules from which the release data of FIG. 1 were obtained contained 1.0002 grams human serum albumin (90.9%) and 0.1001 grams of L-epinephrine (9.1%, free base, Sigma Chemical Company). The crosslinking temperature was 140° C. and the crosslinking time was four hours.

In FIG. 1, the data were obtained by measuring the percent of initial drug concentration in the spherules released with time. In vitro release studies on the epinephrine-containing albumin spherules were carried out in a dynamic fashion using a flow cell technique.

The flow cell consisted of a ⅜″ × 2″ cylindrical glass tube (inside dimensions) containing a Corning Type D sintered glass frit (10–20 micron pore size) at the outlet end. The inlet end was flattened in order to accommodate a small magnetic stirring bar. A clamp and O-ring seal arrangement permitted easy loading of the cell with microspheres and easy disassembly for cleaning purposes. A small disc of filter paper (Amicon Type XM-300) placed over the glass frit at the outlet end prevented any of the microspheres from escaping during the course of the experiment. In a typical release experiment, 5–15 mg of epinephrine-containing microspheres were placed in the cell. The inlet end of the cell was connected via Teflon tubing (⅛″ O.D., 0.085″ I.D.) to an ISCO Model 310 Metering Pump which was used to force phosphate-buffered saline solution (137 mM NaCl, 27 mM KCl, 8 mM NaHPO4, 1 mM KH2PO4) at a pH of 7.6 through the cell at a predetermined constant pumping speed—30.0 ± 1.0 ml per hour. The contents of the cell were vigorously stirred with a magnetic stirrer throughout the course of the release experiment. The drug-containing effluent from the cell passed via Teflon tubing through a cuvette contained in an ultraviolet optical unit (ISCO Type 6) attached to an ISCO Model UA-5 Absorbance Monitor. This instrument provided a strip chart recorder readout of the drug concentration released from the spheres (in terms of optical density) versus time. The stirred flow cell was always kept submerged in a water bath maintained at 37° C.

All of the effluent from each drug release experiment was collected in a graduate cylinder. Spectrophotometric analysis of this effluent on a Beckman DK-2A spectrophotometer according to Beer's Law permitted the determination of the total percent drug released from the microspheres during the time course of the release experiment. Cutting and weighing of the area under the strip chart drug release curve permitted determination of the percent drug released from the microspheres as a function of time.

The following data were obtained:

| | Release Characteristics | | |
|---|---|---|---|
| Time (Minutes) | % Drug Released | % Drug Retained | ln(100c/co) |
| 0 | 0 | 100.0 | 4.605 |
| 4 | 1.5 | 98.5 | 4.590 |
| 8 | 3.2 | 96.8 | 4.572 |
| 12 | 6.0 | 94.0 | 4.543 |
| 16 | 10.2 | 89.8 | 4.498 |
| 20 | 15.1 | 84.9 | 4.441 |
| 24 | 19.7 | 80.3 | 4.386 |
| 28 | 23.8 | 76.2 | 4.333 |
| 32 | 27.5 | 72.5 | 4.283 |
| 36 | 30.7 | 69.3 | 4.238 |
| 40 | 33.7 | 66.3 | 4.194 |
| 44 | 36.4 | 63.6 | 4.153 |
| 48 | 38.8 | 61.2 | 4.114 |
| 52 | 41.0 | 59.0 | 4.077 |
| 56 | 43.0 | 57.0 | 4.043 |
| 60 | 44.9 | 55.1 | 4.009 |
| 64 | 46.6 | 53.4 | 3.978 |
| 68 | 48.2 | 51.8 | 3.947 |
| 72 | 49.7 | 50.3 | 3.918 |
| 76 | 51.1 | 48.9 | 3.891 |
| 80 | 52.3 | 47.7 | 3.865 |
| 88 | 54.6 | 45.4 | 3.815 |
| 96 | 56.5 | 43.5 | 3.774 |
| 104 | 58.0 | 42.0 | 3.738 |
| 112 | 59.3 | 40.7 | 3.707 |
| 120 | 60.3 | 39.7 | 3.681 |
| 132 | 61.6 | 38.4 | 3.647 |
| 144 | 62.7 | 37.3 | 3.618 |
| 156 | 63.5 | 36.5 | 3.597 |

-continued

| | Release Characteristics | | |
|---|---|---|---|
| Time (Minutes) | % Drug Released | % Drug Retained | ln(100c/co) |
| 168 | 64.1 | 35.9 | 3.580 |
| 179.2 | 64.5 | 35.5 | 3.570 |

The values ln(100c/co) were used to determine the rate constant for drug release (K) and the half-time ($t_{\frac{1}{2}}$) of drug release according to the following mathematical analysis.

If it is assumed that the rate of release of the drug from the spherules is first order and hence proportional to the concentration of drug remaining in the spherules, the rate constant can be determined by the equation:

$$-dc/dt = Kc$$

where:
- c = concentration of drug remaining in spheres at time t
- K = rate constant for drug release
- t = time
- $c_o$ = initial concentration of drug at time t = 0

From this equation the final equation for determining the first order release constant (K) was derived as follows:

$$-dc/c = Kdt \tag{1}$$

$$\int_{c_o}^{c} \frac{dc}{c} = - \int_{0}^{t} Kdt \tag{2}$$

$$\ln c - \ln c_o = -Kt \tag{3}$$

$$\ln (c/c_o) = -Kt \tag{4}$$

or $$c/c_o = e^{-Kt}$$

Both sides of the equation are multiplied by 100 to convert the fraction of drug remaining ($c/c_o$) to percent drug remaining ($100c/c_o$).

$$100c/c_o = 100e^{-Kt} \tag{5}$$

If the natural logarithm of both sides of the equation is taken:

$$\ln (100c/c_o) = \ln (\% \text{ drug remaining in spherule}) = -Kt + \ln 100 = -Kt + B(\text{a constant}) \tag{6}$$

$$\ln (100c/c_o) = -Kt + B \tag{7}$$

If first order release behavior is obeyed by the drug-spherule system, a plot of ln ($c/c_o$) or ln ($100c/c_o$) vs. time would be linear with slope $-K$.
At $c = 0.5 c_o$, $$\ln (c/c_o) = \ln (0.5c_o/c_o) = \ln 0.5 = -Kt_{\frac{1}{2}}$$

where $t_{\frac{1}{2}}$ = half time of release = $-\ln 0.5/K$ = 0.693/K

Hence, it is possible to determine both the release rate constant K and $t_{\frac{1}{2}}$ from appropriate plots of ln ($c/c_o$) vs. t.

Plotting the release data in FIG. 1, it was found that the initial 60 minutes of the release curve is quite linear and can be represented by the equation ln ($c/c_o$) = $-Kt$ (in terms of fraction of drug retained by the spherule) or by ln ($100c/c_o$) = $-Kt + B$ (in terms of percent drug retained by the spherule).

Similarly, the latter portions of the release curve (100 to 200 minutes) can be represented with another straight line of differing slope. The ln($c/c_o$) or ln($100c/c_o$) vs. t plots curve in the central portion indicating a shift in release properties from fast to slow as drug release proceeds.

The release data were analyzed according to equation (7) above using a least squares procedure and the "best fit" straight lines through the initial and final portions of the curves determined. The values K and $t_{\frac{1}{2}}$ were determined for the initial and final portions as follows:

$t_{\frac{1}{2}}$ fast $$\ln (100c/c_o) = -0.010921 \, t + 4.650$$

$$K = 1.0921 \times 10^{-2} \text{min}^{-1} \quad t_{\frac{1}{2}} = 0.693/K$$

($t_{\frac{1}{2}}$fast = 63.5 min.)

$t_{\frac{1}{2}}$ slow $$\ln (100 \, c/c_o) = -0.0019155 \, t + 3.900$$

$$K = 1.9155 \times 10^{-3} \text{min}^{-1}$$

($t_{\frac{1}{2}}$ slow = 361.8 min.)

Figure 2:
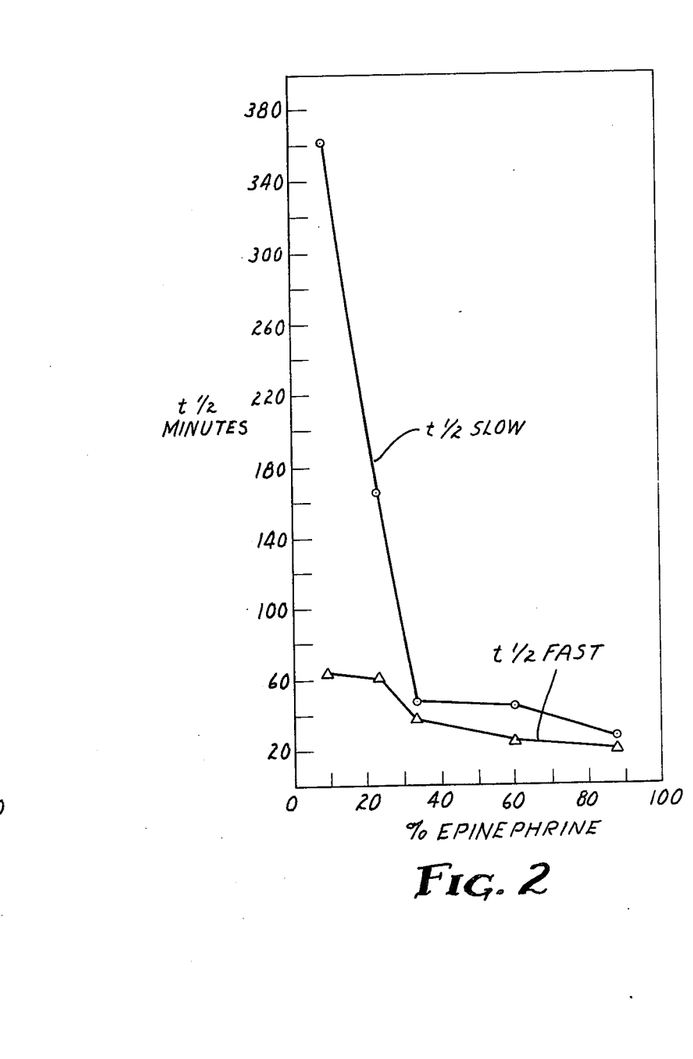
FIG. 2 is a graph showing the effects of drug (epinephrine) concentration on the release characteristics of the spherule.

In FIG. 2, the results of 5 experiments are shown wherein the concentration of epinephrine in spherules was 9.1 (described above), 23.1, 33.3, 60.0 and 87.5 percent respectively. The data used to prepare the graph of FIG. 2 are given below.

EXPERIMENT 2

(23.1% Epi)

Sphere Composition:
1.0003 gm HSA = 76.9% HSA
0.3002 gm l-epinephrine = 23.1% epi
Crosslink Conditions: 140° C., 4 hr.

| | Release Characteristics | | |
|---|---|---|---|
| Time (Minutes) | % Drug Released | % Drug Retained | ln(100 c/co) |
| 0 | 0 | 100.0 | 4.605 |
| 4 | 1.6 | 98.4 | 4.589 |
| 8 | 3.6 | 96.4 | 4.568 |
| 12 | 7.3 | 92.7 | 4.530 |
| 16 | 11.5 | 88.5 | 4.483 |
| 20 | 15.6 | 84.4 | 4.436 |
| 24 | 19.6 | 80.4 | 4.387 |
| 28 | 23.1 | 76.9 | 4.342 |
| 32 | 26.4 | 73.6 | 4.299 |
| 36 | 29.4 | 70.6 | 4.257 |
| 40 | 32.3 | 67.7 | 4.215 |
| 44 | 34.8 | 65.2 | 4.178 |
| 48 | 37.1 | 62.9 | 4.141 |
| 52 | 39.2 | 60.8 | 4.107 |
| 56 | 41.1 | 58.9 | 4.077 |
| 60 | 42.7 | 57.3 | 4.048 |
| 68 | 45.8 | 54.2 | 3.993 |
| 80 | 49.6 | 50.4 | 3.920 |
| 92 | 52.5 | 47.5 | 3.861 |
| 108 | 55.7 | 44.3 | 3.791 |
| 128.8 | 59.0 | 41.0 | 3.714 |

Results of Half-Time Calculations $t_{\frac{1}{2}}$ fast $$\ln (100 \, c/c_o) = -0.011471 \, t + 4.664$$

$$K = 1.1471 \times 10^{-2} \text{min}^{-1}$$

($t_{\frac{1}{2}}$ fast = 60.4 min.)

$t_{\frac{1}{2}}$ slow $$\ln(100\, c/c_o) = -0.004205\, t + 4.251$$

$$K = 4.205 \times 10^{-3} \text{min}^{-1}$$

($t_{\frac{1}{2}}$ slow = 164.8 min.)

EXPERIMENT 3

(33.3% Epi)

Sphere Composition:
 1.0002 gm HSA = 66.7% HSA
 0.5003 gm l-epinephrine = 33.3% epi
Crosslink Conditions: 140° C., 4 hr.

| Time (Minutes) | Release Characteristics | | |
|---|---|---|---|
| | % Drug Released | % Drug Retained | ln(100 c/co) |
| 0 | 0 | 100.0 | 4.605 |
| 4 | 1.9 | 98.1 | 4.586 |
| 8 | 4.1 | 95.9 | 4.564 |
| 12 | 7.0 | 93.0 | 4.533 |
| 16 | 10.9 | 89.1 | 4.490 |
| 20 | 15.3 | 84.7 | 4.439 |
| 24 | 19.9 | 80.1 | 4.384 |
| 28 | 24.5 | 75.5 | 4.324 |
| 32 | 29.4 | 70.6 | 4.257 |
| 36 | 34.1 | 65.9 | 4.189 |
| 40 | 38.5 | 61.5 | 4.120 |
| 44 | 42.8 | 57.2 | 4.047 |
| 48 | 45.8 | 53.2 | 3.973 |
| 52 | 50.8 | 49.2 | 3.897 |
| 56 | 54.4 | 45.6 | 3.820 |
| 60 | 57.8 | 42.2 | 3.743 |
| 64 | 60.7 | 39.3 | 3.670 |
| 68 | 63.6 | 36.4 | 3.596 |
| 72 | 66.1 | 33.9 | 3.523 |
| 76 | 68.6 | 31.4 | 3.447 |
| 80 | 70.8 | 29.2 | 3.375 |
| 84 | 73.0 | 27.0 | 3.297 |
| 88 | 75.0 | 25.0 | 3.221 |
| 96 | 78.5 | 21.5 | 3.070 |
| 104 | 81.6 | 18.4 | 2.913 |
| 112 | 84.2 | 15.8 | 2.761 |
| 120 | 86.3 | 13.7 | 2.617 |
| 132 | 89.0 | 11.0 | 2.395 |
| 144 | 91.2 | 8.8 | 2.176 |
| 156 | 92.7 | 7.3 | 1.983 |
| 168 | 93.9 | 6.1 | 1.808 |
| 177.6 | 94.7 | 5.3 | 1.668 |

Results of Half-Time Calculations $t_{\frac{1}{2}}$ fast $$\ln(100\, c/c_o) = -0.018629\, t + 4.858$$

$$K = 1.8629 \times 10^{-2} \text{min}^{-1}$$

($t_{\frac{1}{2}}$ fast = 37.2 min.)

$t_{\frac{1}{2}}$ slow $$\ln(100\, c/c_o) = -0.014583\, t + 4.258$$

$$K = 1.4583 \times 10^{-2} \text{min}^{-1}$$

($t_{\frac{1}{2}}$ slow = 47.5 min.)

EXPERIMENT 4

(60% Epi)

Sphere Composition:
 0.2003 gm HSA = 40.0% HSA
 0.3002 gm l-epinephrine = 60.0% epi
Crosslink Conditions: 140° C., 4 hr.

| Time (Minutes) | Release Characteristics | | |
|---|---|---|---|
| | % Drug Released | % Drug Retained | ln(100 c/co) |
| 0 | 0 | 100.0 | 4.605 |
| 4 | 6.0 | 94.0 | 4.543 |
| 8 | 12.0 | 88.0 | 4.478 |
| 12 | 19.5 | 80.5 | 4.389 |
| 16 | 28.0 | 72.0 | 4.277 |
| 20 | 36.1 | 63.9 | 4.158 |
| 24 | 43.4 | 56.6 | 4.036 |
| 28 | 50.0 | 50.0 | 3.912 |
| 32 | 55.7 | 44.3 | 3.791 |
| 36 | 60.7 | 39.3 | 3.672 |
| 40 | 64.9 | 35.1 | 3.558 |
| 44 | 68.6 | 31.4 | 3.446 |
| 48 | 71.8 | 28.2 | 3.338 |
| 52 | 74.3 | 25.7 | 3.245 |
| 56 | 76.6 | 23.4 | 3.155 |
| 60 | 78.4 | 21.6 | 3.073 |
| 68 | 81.1 | 18.9 | 2.939 |
| 76 | 82.8 | 17.2 | 2.845 |

Results of Half-Time Calculations $t_{\frac{1}{2}}$ fast $$\ln(100\, c/c_o) = -0.028021\, t + 4.705$$

$$K = 2.8021 \times 10^{-2} \text{min}^{-1}$$

($t_{\frac{1}{2}}$ fast = 24.7 min.)

$t_{\frac{1}{2}}$ slow $$\ln(100\, c/c_o) = -0.015458\, t + 4.008$$

$$K = 1.5458 \times 10^{-2} \text{min}^{-1}$$

($t_{\frac{1}{2}}$ slow = 44.8 min.)

EXPERIMENT 5

(87.5% Epi)

Sphere Composition:
 0.1003 gm HSA = 12.5% HSA
 0.7002 gm l-epinephrine = 87.5% epi
Crosslink Conditions: 140° C., 4 hr.

| Time (Minutes) | Release Characteristics | | |
|---|---|---|---|
| | % Drug Released | % Drug Retained | ln(100 c/co) |
| 0 | 0 | 100.0 | 4.605 |
| 4 | 4.9 | 95.1 | 4.555 |
| 8 | 10.4 | 89.6 | 4.496 |
| 12 | 18.0 | 82.0 | 4.407 |
| 16 | 27.1 | 72.9 | 4.290 |
| 20 | 36.4 | 63.6 | 4.152 |
| 24 | 44.9 | 55.1 | 4.009 |
| 28 | 52.7 | 47.3 | 3.856 |
| 32 | 59.8 | 40.2 | 3.695 |
| 36 | 65.4 | 34.6 | 3.545 |
| 40 | 70.0 | 30.0 | 3.402 |
| 44 | 73.8 | 26.2 | 3.266 |
| 48 | 76.9 | 23.1 | 3.139 |

-continued

| Time (Minutes) | Release Characteristics | | $\ln(100\, c/c_o)$ |
|---|---|---|---|
| | % Drug Released | % Drug Retained | |
| 56 | 81.7 | 18.3 | 2.908 |
| 64 | 85.2 | 14.8 | 2.693 |
| 76 | 88.9 | 11.1 | 2.406 |
| 92 | 92.6 | 7.4 | 2.001 |

Results of Half-Time Calculations $t_{\frac{1}{2}}$ fast $$\ln(100\, c/c_o) = -0.034747\, t + 4.818$$

$$K = 3.4747 \times 10^{-2} \text{min}^{-1}$$

($t_{\frac{1}{2}}$ fast = 19.9 min)

$t_{\frac{1}{2}}$ slow $$\ln(100\, c/c_o) = -0.02562\, t + 4.351$$

$$K = 2.562 \times 10^{-2} \text{min}^{-1}$$

($t_{\frac{1}{2}}$ slow = 27.1 min)

SUMMARY OF BIPHASIC RELEASE DATA FOR EXPERIMENTS 1-5

| Sphere Composition | | t1/2 (Fast) | t1/2 (Slow) |
|---|---|---|---|
| % HSA | % L-epi | | |
| 90.9 | 9.1 | 63.5 min. | 361.8 min. |
| 76.9 | 23.1 | 60.4 min. | 164.8 min. |
| 66.7 | 33.3 | 37.2 min. | 47.5 min. |
| 40.0 | 60.0 | 24.7 min. | 44.8 min. |
| 12.5 | 87.5 | 19.9 min. | 27.1 min. |

It can be seen from FIG. 2 that as drug loading is increased above about 30 percent, biphasic release characteristics are nearly lost, i.e., $t_{\frac{1}{2}}$ (fast) nearly equals $t_{\frac{1}{2}}$ (slow).

The term "biphasic" as used herein to characterize the release of the drug from the spherules, shall apply when the ratio of $t_{\frac{1}{2}}$ (slow)/$t_{\frac{1}{2}}$ (fast) as determined from a ln (100$c/c_o$) vs. time plot is $\geq 2$.

The medicament-containing albumin spherules of the invention may be further illustrated by the following nonlimiting examples.

EXAMPLE 1

This example illustrates typical drug-containing albumin microspherule preparations using heat-crosslinking and chemical crosslinking.

Sample A.–Heat Crosslinking 0.9999 grams of Human Serum Albumin (Sigma, Fraction V, Lot #246-16318) were dissolved in 2.0 ml of deionized water by stirring with a magnetic stirrer. To the dissolved albumin was added 0.1057 grams of the anti-tumor drug 5-fluorouracil (5-FU) (Sigma, Lot #23C-2850) and stirring was continued for an additional 15 minutes. Since the 5-FU did not completely dissolve in the albumin solution, the aqueous mixture was placed in a standard tissue grinder of 10 ml capacity (Ace Glass Co.) and further dispersed to insure homogeneous distribution of the remaining undissolved 5-FU particles throughout the albumin solution.

The mixture was immediately injected with a tuberculin syringe equipped with a 20 gauge hypodermic needle into 500 ml of cottonseed oil (contained in a 600 ml stainless steel beaker) at room temperature while stirring with a 1¼" propeller-type stirrer at approximately 2300 rpm. Stirring rates were measured with a Cole-Parmer tachometer, with the rate of stirring determining to a significant extent the ultimate particle size distribution of the resulting spheres. Stirring was continued while the oil bath temperature was raised with a 500 watt immersion heater to a temperature of 140° C. over a 15 minute time period. The bath was held at this temperature for one hour while stirring was maintained at 2300 rpm.

After this time period, the oil bath and its contents were cooled back to room temperature and the resulting microspheres separated from the oil on Whatman #5 filter paper using vacuum filtration. Final traces of oil were removed from the drug-containing spherules by washing them several times with 300 ml aliquots of heptane.

The above procedure produced human serum albumin (HSA) microspheres containing the anti-tumor agent 5-fluorouracil at a concentration of 9.6% (w/w). The spherules existed as an unagglomerated, free-flowing, light-tan powder with individual microspheres lying in the 10-60 micron range.

Sample B. — Chemical Crosslinking 0.9990 grams of Human Serum Albumin (Sigma Chemical Company) were dissolved in 2.0 ml of deionized water by stirring with a magnetic stirrer. To the dissolved albumin was added 0.1500 grams of L-epinephrine (free base, Sigma) and 0.0725 grams of L(+)Ascorbic Acid (Sigma) and stirring was continued for an additional 15 minutes.

The mixture was then immediately injected with a tuberculin syringe equipped with a 20 gauge hypodermic needle into a spheroidization bath consisting of 500 ml cottonseed oil, 13 ml of n-butanol and 2.0 ml of 25% glutaraldehyde. The bath was contained in a 600 ml stainless steel beaker and was stirred at room temperature with a 1¼" propeller-type stirrer at approximately 1200 rpm. Stirring rates were measured with a Cole-Parmer tachometer. Stirring was continued for four hours during which time the microspheres formed upon injection of the albumin/epinephrine/ascorbic acid solution into the bath were dewatered by the n-butanol and crosslinked by the glutaraldehyde present in the bath.

After this time period, the resulting microspherules were separated from the oil on Whatman #5 filter paper using vacuum filtration. Final traces of oil were removed from the drug-containing spheres by washing them three times with 100 ml aliquots of heptane.

The above procedure produced drug-containing human serum albumin (HSA) microspheres of the following dry-weight composition: HSA = 81.8%; 1-epinephrine = 12.3%; L(+) ascorbic acid = 5.9%. The spherules existed as a free-flowing, unagglomerated yellow-orange powder with individual microspheres lying in the 10-80 micron range.

EXAMPLE 2

In this and the following examples in vitro release studies on drug-containing albumin spherules were carried out in a dynamic fashion using a flow cell technique described hereinabove except the flow cell consisted of a ½" × 2" cylindrical glass tube fitted with a Corning Type D sintered glass frit (10–20 micron pore size) at either end.

This example illustrates the manner in which various heat or chemical crosslinking procedures can be used to adjust the rate of release of the bronchodilator epinephrine from albumin microspheres. The release rate of the drug from the spherules was determined using the method and mathematical analysis described hereinabove.

Sample A

Starting albumin concentration in water: 50 percent (w/v). Spherule composition: 3.1% L(+)-ascorbic acid, 88.1% human serum albumin (HSA), 8.8% epinephrine (free base). Crosslink conditions: 115° C. in cottonseed oil bath for one (1) hour.

RELEASE CHARACTERISTICS

| Time (Minutes) | Percent Drug Released | Percent Drug Retained |
| --- | --- | --- |
| 0 | 0 | 100 |
| 3 | 4.3 | 95.7 |
| 6 | 11.0 | 89.0 |
| 9 | 23.4 | 76.6 |
| 12 | 34.6 | 65.4 |
| 15 | 38.1 | 61.9 |
| 18 | 51.5 | 48.5 |
| 21 | 56.7 | 43.3 |
| 24 | 60.8 | 39.2 |
| 27 | 65.5 | 34.5 |
| 30 | 68.6 | 31.4 |
| 36 | 74.5 | 25.5 |
| 42 | 78.5 | 21.5 |
| 48 | 81.4 | 18.6 |
| 63 | 86.4 | 13.6 |
| 78 | 89.3 | 10.7 |
| 208 | 94.7 | 5.3 |

Sample B

Starting albumin concentration: 50 percent (w/v). Spherule composition: 87.5% HSA, 8.9% epinephrine, 3.6% L(+)-ascorbic acid. Crosslink conditions: 120° C. in cottonseed oil bath for six (6) hours.

RELEASE CHARACTERISTICS

| Time (Minutes) | Percent Drug Released | Percent Drug Retained |
| --- | --- | --- |
| 0 | 0 | 100 |
| 3 | 7.5 | 92.5 |
| 6 | 17.1 | 82.9 |
| 9 | 25.5 | 74.5 |
| 12 | 34.3 | 65.7 |
| 15 | 41.3 | 58.7 |
| 18 | 47.4 | 52.6 |
| 21 | 52.2 | 47.8 |
| 27 | 59.1 | 40.9 |
| 33 | 64.2 | 35.8 |
| 42 | 69.2 | 30.8 |
| 57 | 73.6 | 26.4 |
| 72 | 76.0 | 24.0 |
| 102 | 78.9 | 21.1 |
| 154 | 81.6 | 18.4 |

Sample C

Starting albumin concentration: 50 percent (w/v). Spherule composition: 86.9% HSA, 8.7% epinephrine, 4.4% L(+) ascorbic acid.

Crosslink conditions: 130° C. in cottonseed oil bath for six (6) hours.

RELEASE CHARACTERISTICS

| Time (Minutes) | Percent Drug Released | Percent Drug Retained |
| --- | --- | --- |
| 0 | 0 | 100 |
| 3 | 7.8 | 92.2 |
| 6 | 18.0 | 82.0 |
| 9 | 26.2 | 73.8 |
| 12 | 33.2 | 66.8 |
| 15 | 38.4 | 61.6 |
| 18 | 42.1 | 57.9 |
| 21 | 45.8 | 54.2 |
| 27 | 51.2 | 48.8 |
| 33 | 56.2 | 43.8 |
| 48 | 63.5 | 36.5 |
| 66 | 70.8 | 29.2 |

Sample D

Starting albumin concentration: 50 percent (w/v). Spherule composition: 87.5% HSA, 8.8% epinephrine, 3.7% L(+) ascorbic acid.

Crosslink conditions: 145° C. in cottonseed oil bath for six (6) hours.

RELEASE CHARACTERISTICS

| Time (Minutes) | Percent Drug Released | Percent Drug Retained |
| --- | --- | --- |
| 0 | 0 | 100 |
| 4 | 2.4 | 97.6 |
| 7 | 6.1 | 93.9 |
| 10 | 10.2 | 89.8 |
| 13 | 13.9 | 86.1 |
| 16 | 16.4 | 83.6 |
| 22 | 20.8 | 79.2 |
| 34 | 25.0 | 75.0 |
| 44 | 30.7 | 69.3 |

Sample E

Starting albumin concentration: 50 percent (w/v). Spherule composition: 87.8% HSA, 8.9% epinephrine: 3.3% L(+) ascorbic acid. Crosslink conditions: 165° C. in cottonseed oil for six (6) hours.

RELEASE CHARACTERISTICS

| Time (Minutes) | Percent Drug Released | Percent Drug Retained |
| --- | --- | --- |
| 0 | 0 | 100 |
| 3 | 1.0 | 99.0 |
| 6 | 2.3 | 97.7 |
| 9 | 4.0 | 96.0 |
| 12 | 5.2 | 94.8 |
| 15 | 6.3 | 93.7 |
| 18 | 7.6 | 92.4 |
| 21 | 8.2 | 91.8 |
| 27 | 9.5 | 90.5 |
| 48 | 12.4 | 87.6 |
| 78 | 14.8 | 85.2 |
| 158 | 17.7 | 82.3 |

Sample F

Starting albumin concentration: 50 percent (w/v). Spherule composition: 81.8% HSA, 12.3% epinephrine, 5.9% L(+) ascorbic acid. Crosslink conditions: Four (4) hours in 500 ml cottonseed oil containing 13 ml n-butanol and 2.0 ml 25% glutaraldehyde.

| RELEASE CHARACTERISTICS | | |
|---|---|---|
| Time (Minutes) | Percent Drug Released | Percent Drug Retained |
| 0 | 0 | 100 |
| 5 | 2.6 | 97.4 |
| 8 | 6.5 | 93.5 |
| 11 | 11.2 | 88.8 |
| 14 | 13.6 | 86.4 |
| 17 | 16.0 | 84.0 |
| 20 | 18.0 | 82.0 |
| 23 | 19.3 | 80.7 |
| 26 | 21.0 | 79.0 |
| 44 | 26.7 | 73.3 |
| 59 | 29.3 | 70.7 |
| 74 | 30.1 | 69.9 |
| 176 | 32.8 | 67.2 |

As illustrated by samples A–E, increasing the time and temperature of heat crosslinking reduces both the rate at which epinephrine is released from albumin spherules and the total amount of drug released from the spherules by simple diffusion. The remainder of the drug entrapped in the spherule would presumably be released upon degradation of the spherule within the body. Sample A (115° C., 1 hour), for example, releases nearly 50% of the entrapped drug in one hour, whereas the more heavily crosslinked sample E (165° C., 6 hours) releases less than 20% of the entrapped drug in 3 hours. These samples thus illustrate how choice of the time and temperature of crosslinking can produce spherules which release entrapped drug at some predetermined rate and amount.

Note also in sample F that a four hour glutaraldehyde crosslinking treatment is about equivalent to a six hour heat treatment at 140°–150° C.

The release data obtained with samples A–F were analyzed mathematically to determine the rate constant for drug release (K) and the half-time ($t\frac{1}{2}$) of drug release. The results are summarized below:

| Sample | K (Fast) | t1/2 (Fast) | B (Fast) | K (Slow) | t1/2 (Slow) | B (Slow) |
|---|---|---|---|---|---|---|
| A | $37.9 \times 10^{-3} min^{-1}$ | 18.3 min. | 4.63 | $6.07 \times 10^{-3} min^{-1}$ | 114.2 min. | 2.92 |
| B | $32.67 \times 10^{-3} min^{-1}$ | 21.2 min. | 4.59 | $3.18 \times 10^{-3} min^{-1}$ | 217.9 min. | 3.39 |
| C | $25.37 \times 10^{-3} min^{-1}$ | 27.3 min. | 4.55 | Insufficient data | Insufficient data | — |
| D | $9.09 \times 10^{-3} min^{-1}$ | 76.2 min. | 4.60 | Insufficient data | Insufficient data | — |
| E | $3.92 \times 10^{-3} min^{-1}$ | 176.7 min. | 4.60 | $0.55 \times 10^{-3} min^{-1}$ | 1271.6 min. | 4.49 |
| F | $9.70 \times 10^{-3} min^{-1}$ | 71.4 min. | 4.61 | $0.41 \times 10^{-3} min^{-1}$ | 1686.1 min. | 4.28 |

EXAMPLE 3

Serum albumin microspheres containing the antitumor drug 5-fluorouracil (5-FU) were prepared and the release of the drug from the spherules was determined according to the method of Example 2. The results are shown in the following tables:

Sample A

Starting albumin concentration: 50 percent (w/v)
sphere composition: 90.0 percent HSA, 9.1 percent 5-FU
crosslink conditions: one (1) hour in cottonseed oil at 100° C.

| RELEASE CHARACTERISTICS | | |
|---|---|---|
| Time (Minutes) | Percent Drug Released | Percent Drug Retained |
| 0 | 0 | 100 |
| 1 | 4.4 | 95.6 |
| 4 | 23.2 | 76.8 |
| 7 | 42.7 | 57.3 |
| 10 | 54.7 | 45.3 |
| 13 | 63.4 | 36.6 |
| 16 | 70.1 | 29.9 |
| 19 | 75.9 | 24.1 |
| 25 | 83.4 | 16.6 |
| 31 | 88.3 | 11.7 |

Sample B

Starting albumin concentration: 50 percent (w/v)
sphere composition: 90.4 percent HSA, 9.6 percent 5-FU
crosslink conditions: one (1) hour in cottonseed oil at 140° C.

| RELEASE CHARACTERISTICS | | |
|---|---|---|
| Time (Minutes) | Percent Drug Released | Percent Drug Retained |
| 0 | 0 | 100 |
| 2 | 2.3 | 97.7 |
| 5 | 9.0 | 91.0 |
| 8 | 15.5 | 84.5 |
| 11 | 20.0 | 80.0 |
| 14 | 22.5 | 77.5 |
| 17 | 24.2 | 75.8 |
| 20 | 25.5 | 74.5 |
| 100 | 31.4 | 68.6 |

EXAMPLE 4

This example illustrates the release characteristics of the antitumor drug 6-mercaptopurine (6-MP) from human serum albumin spherules as determined by the method of Example 2.

Starting albumin concentration: 50 percent (w/v)
sphere composition: 83.4 percent HSA, 16.6 percent 6-MP
crosslink conditions: one (1) hour in cottonseed oil at 140° C.

| RELEASE CHARACTERISTICS | | |
|---|---|---|
| Time (Minutes) | Percent Drug Released | Percent Drug Retained |
| 0 | 0 | 100 |
| 4 | 2.1 | 97.9 |
| 7 | 5.8 | 94.2 |
| 10 | 9.6 | 90.4 |
| 13 | 12.3 | 87.7 |
| 16 | 14.8 | 85.2 |
| 19 | 16.7 | 83.3 |
| 25 | 20.3 | 79.7 |

-continued

| RELEASE CHARACTERISTICS | | |
|---|---|---|
| Time (Minutes) | Percent Drug Released | Percent Drug Retained |
| 40 | 26.6 | 73.4 |
| 55 | 31.4 | 68.6 |
| 70 | 34.8 | 65.2 |
| 100 | 39.5 | 60.5 |
| 130 | 41.6 | 58.4 |
| 148 | 44.4 | 55.6 |

EXAMPLE 5

This example illustrates the release characteristics of the antitumor drug 6-thioguanine from human serum albumin spherules as determined by the method of Example 2.

Starting concentration of albumin: 50 percent (w/v)
sphere composition: 82.2 percent HSA, 17.8 percent 6-thioguanine
crosslink conditions: one (1) hour in cottonseed oil at 123° C.

| RELEASE CHARACTERISTICS | | |
|---|---|---|
| Time (Minutes) | Percent Drug Released | Percent Drug Retained |
| 0 | 0 | 100 |
| 7 | 1.2 | 98.8 |
| 10 | 2.3 | 97.7 |
| 13 | 3.3 | 96.7 |
| 16 | 4.6 | 95.4 |
| 19 | 6.5 | 93.5 |
| 22 | 7.7 | 92.3 |
| 25 | 9.1 | 90.9 |
| 28 | 10.4 | 89.6 |
| 34 | 13.0 | 87.0 |
| 40 | 15.2 | 84.8 |
| 55 | 20.3 | 79.7 |
| 85 | 29.7 | 70.3 |
| 115 | 37.7 | 62.3 |
| 145 | 43.0 | 57.0 |
| 175 | 47.9 | 52.1 |
| 412 | 55.0 | 45.0 |

EXAMPLE 6

ANTITUMOR AGENTS

A first order kinetic analysis of the release data in Examples 3–5 was carried out according to the mathematical procedure outlined herebefore. The rate parameters obtained are tabulated below.

| Example | K (Fast) | $t_{\frac{1}{2}}$ (Fast) | B (Fast) | K (Slow) | $t_{\frac{1}{2}}$ (Slow) | B (Slow) |
|---|---|---|---|---|---|---|
| 3A (100° C., 1 Hr.) | $76.64 \times 10^{-3}$ Min.$^{-1}$ | 9.0 Min. | 4.61 | $60.17 \times 10^{-3}$ Min.$^{-1}$ | 11.5 Min. | 4.32 |
| 3B (140° C., 1 Hr.) | $19.51 \times 10^{-3}$ Min.$^{-1}$ | 35.5 Min. | 4.61 | $1.13 \times 10^{-3}$ Min.$^{-1}$ | 615 Min. | 4.34 |
| 4 (140° C., 1 Hr.) | $9.66 \times 10^{-3}$ Min.$^{-1}$ | 71.7 Min. | 4.61 | $2.13 \times 10^{-3}$ Min.$^{-1}$ | 325 Min. | 4.33 |
| 5 (123° C., 1 Hr.) | $4.27 \times 10^{-3}$ Min.$^{-1}$ | 162.3 Min. | 4.62 | $0.78 \times 10^{-3}$ Min.$^{-1}$ | 886 Min. | 4.13 |

Comparing the K and $t_{\frac{1}{2}}$ values of Examples 3A and 3B, the albumin spherules containing 5-FU which were heated at 100° C. for one hour show very little biphasic character, whereas the 5-FU sample crosslinked at 140° C. for one hour exhibits strong biphasic character. The $t_{\frac{1}{2}}$ (fast) and $t_{\frac{1}{2}}$ (slow) values are greatly increased as the temperature of crosslinking is raised.

Both 6-MP and 6-thioguanine entrapped in albumin spherules exhibit biphasic release characteristics as shown in Examples 4 and 5. Both $t_{\frac{1}{2}}$ (fast) and $t_{\frac{1}{2}}$ (slow) values for 6-MP are faster than the corresponding values for 6-thioguanine, even though 6-MP was heated at 140° C. vs. 123° C. for 6-thioguanine. The longer $t_{\frac{1}{2}}$ values for 6-thioguanine no doubt reflect its lesser water solubility as compared to 6-MP.

The following examples illustrate that the processes used to prepare the spherules of the invention do not destroy the activity of the entrapped drug.

EXAMPLE 7

About 20–25 mg. of human serum albumin spherules prepared from 50 percent HSA solutions containing the bronchodilator drug epinephrine were dispersed in 10 ml. of an aqueous solution of HCl (pH 3.0) and magnetically stirred for one hour to release significant quantities of entrapped drug. The spherules were centrifuged and separated from the supernatant which was analyzed spectrophotometrically to determine the concentration of released drug. These supernatant samples were then subjected to in vitro efficacy evaluation using the following guinea pig tracheal tissue test.

Guinea pig tracheal tissue was suspended in Krebs solution at 38° C. and allowed to equilibrate. The tissue was connected to a strain gauge transducer and output recorder in such a way that changes in the length of the tissue caused by its contraction or relaxation could be measured. Addition of small amounts of an agonist such as histamine (~2 micrograms/ml.) caused strong contraction of the tissue. Addition of pure epinephrine or of the supernatant solutions containing epinephrine derived from the albumin spherules caused relaxation of the tissue. The concentration of released epinephrine (in micrograms/ml.) required to cause relaxation of histamine-contracted tracheal tissue was determined and compared with an epinephrine control evaluated in similar fashion to assess activity of the released epinephrine.

The data obtained from the guinea pig tracheal tissue tests is shown in the following table.

| | Sphere Sample Composition From Which Drug Was Obtained | Dose of Drug Added to Tracheal Tissue Bath (micrograms/ml.) | Percent Relaxation of Tracheal Tissue |
|---|---|---|---|
| A | pure l-epinephrine control | 0.1 – 0.2 | 100 |
| B | HSA = 78%, epinephrine (epi) = 12.5%, L(+) − ascorbic acid = 9.5%, crosslink conditions: 68° C., 2.5 hours | 0.1 | 100 |

-continued

| Sphere Sample Composition From Which Drug Was Obtained | | Dose of Drug Added to Tracheal Tissue Bath (micrograms/ml.) | Percent Relaxation of Tracheal Tissue |
|---|---|---|---|
| C | HSA = 73.8%, epi = 21.2%, L(+) − ascorbic acid = 5.0%, crosslink conditions: 100° C., 1 hour | 0.1 | 100 |
| D | HSA = 86.9%, epi = 8.7% L(+) − ascorbic acid = 4.4% crosslink conditions: 100° C., 6 hours. | 0.01 0.02 0.03 | 25 75 100 |
| E | HSA = 87.3%, epi = 8.8%, L(+) − ascorbic acid = 3.9% crosslink conditions: 110° C., 1 hour | 0.01 0.02 0.03 0.05 0.10 | 27 53 73 82 100 |
| F | HSA = 87.7%, epi = 8.8%, L(+) − ascorbic acid = 3.5% crosslink conditions: 110° C., 4 hours | 0.01 0.02 0.03 0.05 0.10 | 6 31 53 71 100 |
| G | HSA = 88.1%, epi = 8.8%, L(+) − ascorbic acid = 3.1% crosslink conditions: 115° C., 1 hour | 0.01 0.02 0.03 0.05 0.10 | 32 72 84 91 100 |
| H | HSA = 87.5%, epi = 8.8%, L(+) − ascorbic acid = 3.7% crosslink conditions: 120° C., 6 hours | 0.01 0.02 0.03 0.05 | 25 75 92 100 |
| I | HSA = 86.9%, epi = 8.7%, L(+) − ascorbic acid = 4.4% crosslink conditions: 130° C., 6 hours. | 0.01 0.02 0.03 0.04 0.10 0.20 | 0 7 22 37 67 100 |
| J | HSA = 87.5%, epi 8.8%, L(+) − ascorbic acid = 3.7% crosslink conditions: 145° C., 6 hours | 0.01 0.03 0.04 0.05 0.10 0.20 0.30 0.40 | 0 7 11 19 33 67 89 100 |
| K | HSA = 87.8%, epi = 8.9%, L(+) − ascorbic acid = 3.3% crosslink conditions: 165° C., 6 hours | 0.01 0.04 0.10 0.20 0.30 0.40 0.50 | 0 10 30 50 60 80 100 |
| L | HSA = 81.8%, epi = 12.3%, L(+) − ascorbic acid = 5.9% crosslink conditions: 4 hours in 500 ml. cottonseed oil containing 13 ml. n-butanol and 2.0 ml. 25% glutaraldehyde; 25° C. | 0.1 | 100 |
| M | HSA = 67.3%, epi = 20.2%, L(+) − ascorbic acid = 12.5% crosslink conditions: 4 hours in 500 ml. cottonseed oil containing 13 ml. n- | 1.4 2.8 | 0 0 |

| Sphere Sample Composition From Which Drug Was Obtained | Dose of Drug Added to Tracheal Tissue Bath (micrograms/ml.) | Percent Relaxation of Tracheal Tissue |
|---|---|---|
| butanol and 2.0 ml. 37% formaldehyde; 25° C. | | |

As illustrated in Samples A–K above, there is some loss of activity of the epinephrine with increasing crosslinking temperatures. No significant activity loss (by comparison with the pure epinephrine control) occurs until the crosslinking temperature exceeds 130° C. Surprisingly, however, even after crosslinking the spherules at 165° C. for 6 hours, significant epinephrine activity remains. Thus, even high-temperature crosslinked microspheres are efficacious and suitable for parenteral injection into humans.

Epinephrine entrapped in HSA spherules crosslinked with glutaraldehyde retains essentially full activity. In Example 2, it was shown that glutaraldehyde crosslinking for 4 hours is about equivalent to heat crosslinking for 6 hours at 140° C.–150° C. Since there appears to be little if any activity loss associated with glutaraldehyde crosslinking (as compared to slight activity loss with 140° C.–150° C. heat crosslinking), the chemical crosslinking technique might be preferred for epinephrine if more tightly crosslinked spheres are desired.

Formaldehyde is not the crosslinking agent of choice for epinephrine - containing spherules. However, formaldehyde may be used to crosslink spherules containing other drugs, e.g. 5-fluorouracil, without impairing drug activity.

EXAMPLE 8

The procedure of Example 7 was repeated using human serum albumin spherules containing the bronchodilator salbutamol. The results are shown in the following table:

| | Spherule Sample Composition | Dose (Micrograms/ml) | % Relaxation |
|---|---|---|---|
| | SALBUTAMOL - CONTAINING HSA MICROSPHERES | | |
| A | Salbutamol control | 0.1 | 100 |
| B | HSA = 88.5%, Salbutamol = 6.3% L(+) — ascorbic acid = 4.6% crosslink conditions: 115° C., 1 hr. | 0.1 | 100 |
| C | HSA = 86.1%, Salbutamol = 7.9% L(+) — ascorbic acid = 6.0% crosslink conditions: 4 hrs. in 500 ml cottonseed oil containing 13 ml n-butanol and 2.0 ml 25% glutaraldehyde; 25° C | 1.0 | 100 |

Although heat crosslinking at 115° C. for 1 hour does not appear to affect the activity of salbutamol, glutaraldehyde crosslinking appears to lower the activity of the drug.

EXAMPLE 9

The procedure of Example 7 was repeated using human serum albumin spherules containing the bronchodilator terbutaline. The results are shown in the following table:

| | Spherule Sample Composition | Dose (micrograms/ml) | % Relaxation |
|---|---|---|---|
| A | Pure Terbutaline control | 0.1 - 1.0 | 100 |
| B | HSA = 78.7%, Terbutaline = 11.7% L(+) — ascorbic acid = 9.6% crosslink conditions: 68° C., 2.5 hrs. | 0.1 - 1.0 | 100 |
| C | HSA = 82.9% Terbutaline = 12.5% L(+) — ascorbic acid = 4.6% crosslink conditions: 105° C., 1 hr. | 0.1 - 1.0 | 100 |
| D | HSA = 81.5% Terbutaline = 12.3% L(+) — ascorbic acid = 6.2% crosslink conditions: 4 hours in 500 ml cottonseed oil containing 13 ml n-butanol and 2.0 ml 25% glutaraldehyde; 25° C. | 0.1 - 1.0 | 100 |

It is evident from the above that none of the heat or chemical crosslinking procedures utilized has any deleterious effect on the bronchodilator activity of terbutaline.

EXAMPLE 10

The activity of human serum albumin spherules containing the antitumor drug 5-fluorouracil was assayed by using a mouse L-Cell test.

L-676 mouse embryo fibroblasts were grown and maintained in liquid shake cultures of Swims-67G medium fortified by the addition of 5% fetal calf serum and supplemented with 1%, 200 millimolar glutamine.

Free drugs (without a carrier) used as controls were solubilized in either sterile distilled water or acetone and then added to the growth medium. When acetone was used as a drug solvent, concentration levels were always low enough to remain non-toxic to the growth medium.

Drug containing HSA spherules were resuspended in growth medium. A sonifying water bath was employed to aid in suspension. Microscopic examination did not reveal any sphere destruction.

A 10% (v/v) inoculum of L-cells was employed in a final volume of 20 ml of growth medium containing suspended drug-containing microspheres or free control drug. Results were read by direct cell count after incubation on a rotary shaker (200 rpm) at 37° C. for 3 days, and expressed as percent inhibition of growth vs. control (untreated) cell cultures. All tests were performed in duplicate.

| % INHIBITION OF L-CELL GROWTH AT 72 HOURS | | | | |
|---|---|---|---|---|
| | Concentration of Drug in L-Cell Suspension (micrograms/ml) | | | |
| Anti-Tumor Agent | 1 | 10 | 50 | 100 |
| Pure 5-fluorouracil (5-FU) control (not contained in spheres) | 67% | 88% | 93% | 93% |

| 5-FU IN VARIOUS CROSSLINKED ALBUMIN MICROSPHERES | | |
|---|---|---|
| Sample A | Concentration of Drug in Spheres (micrograms 5-FU/ml cell culture) | % L-Cell Inhibition |
| Sphere composition: 99% HSA, 1% 5-FU | 0.3 | 39 |
| Crosslink conditions: 24 hours in 500 ml cottonseed oil containing 13 ml n-butanol and 2.0 ml 37% formaldehyde at 25° C. | 3.0 | 99 |
| Sample B | | |
| Sphere composition: 86.6% HSA, 13.4% 5-FU | 4.0 | 98 |
| Crosslink conditions: 24 hours in 500 ml cottonseed oil containing 13 ml n-butanol and 2.0 ml 37% formaldehyde at 25° C. | | |
| Sample C | | |
| Sphere composition: 98.7% HSA 1.3% 5-FU | 0.4<br>3.9 | 47<br>95 |
| Crosslink conditions: 140° C. in cottonseed oil bath for two hours | | |
| Sample D | | |
| Sphere composition: 86.9% HSA, 13.1% 5-FU (higher concentration than in Sample C) | 3.9 | 99 |
| Crosslink conditions: 140° C. in cottonseed oil bath for two hours | | |
| Sample E | | |
| Sphere composition: 83.1% HSA, 16.9% 5-FU | 5.1 | 100 |
| Crosslink conditions: 5.5 hours in 500 ml cottonseed oil containing 13 ml n-butanol and 2.0 ml 37% formaldehyde at 25° C. | | |

These data demonstrate that both heat and chemically crosslinked albumin spherules containing 5-FU maintain high activity after the drug incorporation step.

EXAMPLES 11–17

Using the method described in Example 10, albumin spherules containing other antitumor drugs were tested for retained activity in comparison to free antitumor drugs. The results are shown in the following table:

| Example No. | Spherule Composition | Concentration of Drug in Spherule (μg drug/ml Cell Culture) | % L-Cell Inhibition |
|---|---|---|---|
| 11<br>Chlorambucil | a) 95.5% HSA,<br>4.5% Chlorambucil<br>Crosslink conditions: 24 hours in 500 ml cottonseed oil containing 13 ml n-butanol and 2.0 | 1.35<br>13.5 | 28<br>89 |

-continued

| Example No. | Spherule Composition | Concentration of Drug in Spherule (µg drug/ml Cell Culture) | % L-Cell Inhibition |
|---|---|---|---|
| | ml 37% formaldehyde | | |
| | b) Control-free Chlorambucil | 1 | 0 |
| | | 10 | 68 |
| | | 50 | 97 |
| 12 Hydrocortisone Acetate | a) 83.9% HSA 16.1% Hydrocortisone Acetate Crosslink conditions: 120° C., 1 hour in cottonseed oil | 4.8 | 88 |
| | b) Control-free Hydrocortisone Acetate | 1.0 | 0 |
| | | 10.0 | 0 |
| | | 50.0 | 73 |
| | | 100.0 | 88 |
| 13 Colchicine | a) 83.1% HSA 16.9% Colchicine Crosslink conditions: 143° C., 1 hour in cottonseed oil | 5.1 | 99 |
| | b) 83.4% HSA 16.6% Colchicine Crosslink conditions 5.5 hours in 500 ml cottonseed oil containing 13 ml n-butanol and 2.0 ml 25% glutaraldehyde | 5.0 | 93 |
| | c) Control-free Colchicine | 1.0 | 91 |
| | | 10.0 | 99 |
| 14 Hydroxyurea | a) 86.4% HSA 16.6% Hydroxyurea Crosslink conditions: 125° C., 1 hour in cottonseed oil | 5.0 | 25 |
| | b) Control-free Hydroxyurea | 1.0 | 0 |
| | | 10.0 | 22 |
| 15 6-Thioguanine | a) 82.2% HSA 17.8% 6-Thioguanine Crosslink conditions: 123° C., 1 hour in cottonseed oil | 5.3 | 96 |
| | b) Control-free 6-Thioguanine | 1.0 | 65 |
| | | 10.0 | 88 |
| | | 50.0 | 92 |
| 16 Busulfan | a) 83.2% HSA 16.8% Busulfan Crosslink conditions: 115° C., 1 hour in cottonseed oil | 25.0 | 56 |
| | b) Control-free Busulfan | 25.0 | 69 |
| 17 6-Mercaptopurine | a) 83.0% HSA 17.0% 6-Mercaptopurine Crosslink conditions: 130° C., 1 hour in cottonseed oil | 50 | 95 |
| | b) Control-free 6-Mercaptopurine | 50 | 94 |

What is claimed is:

1. A therapeutic composition for controlling the release of drugs comprising solid spherules of serum albumin having homogeneously entrapped therein from 5 to 30 percent by weight of the spherule of an organic medicament which is at least 0.01 percent water soluble at 37° C., which spherules have been crosslinked by a process selected from the group consisting of: (a) heating at 110° to 180° C. for at least twenty minutes and (b) exposing to at least one chemical crosslinking agent which does not substantially affect the activity of said medicament for sufficient time to crosslink the albumin to a degree equivalent to heating at 110° to 180° C. for at least twenty minutes, and when placed in an aqueous medium, said medicament is released in a biphasic manner.

2. A composition according to claim 1 wherein the medicament is an antitumor agent.

3. A composition according to claim 2 wherein the medicament is 6-mercaptopurine.

4. A composition according to claim 2 wherein the medicament is 5-fluorouracil.

5. A composition according to claim 2 wherein the medicament is 6-thioguanine.

6. A composition according to claim 2 wherein the medicament is hydroxyurea.

7. A composition according to claim 2 wherein the medicament is colchicine.

8. A composition according to claim 2 wherein the medicament is chlorambucil.

9. A composition according to claim 2 wherein the medicament is busulfan.

10. A composition according to claim 1 wherein the medicament is a bronchodilator.

11. A composition according to claim 10 wherein the medicament is epinephrine.

12. A composition according to claim 10 wherein the medicament is salbutamol.

13. A composition according to claim 10 wherein the medicament is terbutaline.

14. A composition according to claim 1 dispersed in pharmaceutically acceptable extending medium suitable for intravascular injection.

15. A method of treating a disease state in an animal by intravascular injection of a therapeutic composition according to claim 1.

16. A process for preparing solid serum albumin spherules having a medicament homogeneously entrapped therein comprising injecting an aqueous solution of said albumin having said medicament dispersed therein into an agitated vegetable oil bath containing a lipophilic drying alcohol and a crosslinking agent which does not substantially affect the activity of said medicament selected from the group consisting of glutaraldehyde and formaldehyde.

17. A therapeutic composition for controlling the release of drugs comprising solid spherules of serum albumin having homogeneously entrapped therein from 5 to 30 percent by weight of the spherule of an organic medicament which is at least 0.01 percent water soluble at 37° C., which spherules have been crosslinked by heating at 110° to 180° C. for at least twenty minutes during preparation to crosslink the albumin, and when placed in an aqueous medium, said medicament is released from said spherules in a biphasic manner.

18. A therapeutic composition for controlling the release of drugs comprising solid spherules of serum albumin having homogeneously entrapped therein from 5 to 30 percent by weight of the spherule of an organic medicament which is at least 0.01 percent water soluble at 37° C., which spherules have been exposed to at least one chemical crosslinking agent which does not substantially affect the activity of the medicament to crosslink the albumin to a degree equivalent to that achieved by heating at 110° to 180° C. for at least twenty minutes, and when placed in an aqueous medium, said medicament is released from said spherules in a biphasic manner.

* * * * *

UNITED STATES PATENT AND TRADEMARK OFFICE
CERTIFICATE OF CORRECTION

PATENT NO. : 4,147,767
DATED : April 3, 1979
INVENTOR(S) : Anthony F. Yapel, Jr.

It is certified that error appears in the above—identified patent and that said Letters Patent is hereby corrected as shown below:

Column 13, line 34, "45.8" should read -- 46.8 --;

Column 19, line 39, "37.9. . ." should read -- 37.94. . . --;

Column 19, line 65, "90.0 percent" should read -- 90.9 percent --.

Signed and Sealed this

Fourteenth Day of July 1981

[SEAL]

Attest:

GERALD J. MOSSINGHOFF

Attesting Officer

Commissioner of Patents and Trademarks